(12) United States Patent
Connolly

(10) Patent No.: US 9,533,125 B2
(45) Date of Patent: Jan. 3, 2017

(54) BALLOON CATHETER AND METHOD OF MANUFACTURE

(71) Applicant: BOSTON SCIENTIFIC SCIMED, INC., Maple Grove, MN (US)

(72) Inventor: Patrick Connolly, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 266 days.

(21) Appl. No.: 14/502,449

(22) Filed: Sep. 30, 2014

(65) Prior Publication Data

US 2015/0091221 A1 Apr. 2, 2015

Related U.S. Application Data

(60) Provisional application No. 61/885,270, filed on Oct. 1, 2013.

(51) Int. Cl.
*A61M 25/10* (2013.01)
*B29C 49/42* (2006.01)
(Continued)

(52) U.S. Cl.
CPC ...... *A61M 25/1029* (2013.01); *B29C 47/0023* (2013.01); *B29C 47/0054* (2013.01); *B29C 49/4252* (2013.01); *A61M 25/1034* (2013.01); *A61M 2025/1065* (2013.01); *B29C 49/04* (2013.01); *B29C 49/20* (2013.01); *B29C 2049/2047* (2013.01); *B29K 2105/258* (2013.01); *B29L 2031/7543* (2013.01)

(58) Field of Classification Search
CPC ............ B29C 49/4252; B29C 49/4273; B29C 2049/2047; B29C 2049/021; B29L 2031/7543; A61M 25/1029; A61M 25/1034; A61M 2025/1065
See application file for complete search history.

(56) References Cited

U.S. PATENT DOCUMENTS 3,833,004 A 9/1974 Vazquez et al.
4,093,484 A * 6/1978 Harrison ........... A61M 25/1027
156/244.13

(Continued)

FOREIGN PATENT DOCUMENTS

EP 0351734 A 1/1990
EP 359489 A2 3/1990
(Continued)

*Primary Examiner* — Robert B Davis
(74) *Attorney, Agent, or Firm* — Seager, Tufte & Wickhem LLP

(57) ABSTRACT

A method of manufacturing a balloon catheter in which an extruded tubular balloon parison is attached to a component of a catheter shaft prior to blow molding a balloon from the extruded tubular balloon parison. A distal end region of the tubular balloon parison is attached to the outer surface of the elongate catheter shaft component to form a distal bond region between the tubular balloon parison and the catheter shaft component, and then the assembly is positioned in a balloon mold. An annular space between an inner surface of the tubular balloon parison and the outer surface of the elongate tubular member is pressurized to expand the tubular balloon parison in the cavity of the balloon mold to form an inflatable balloon.

20 Claims, 15 Drawing Sheets

(51) Int. Cl.
*B29C 47/00* (2006.01)
*B29C 49/20* (2006.01)
*B29C 49/04* (2006.01)
*B29K 105/00* (2006.01)
*B29L 31/00* (2006.01)

(56) References Cited

U.S. PATENT DOCUMENTS

| | | | |
|---|---|---|---|
| 4,147,169 | A | 4/1979 | Taylor |
| 4,863,424 | A | 9/1989 | Blake et al. |
| 4,990,138 | A | 2/1991 | Bacich et al. |
| 5,074,845 | A | 12/1991 | Miraki et al. |
| 5,304,199 | A | 4/1994 | Myers |
| 5,951,513 | A | 9/1999 | Miraki |
| 6,206,868 | B1 | 3/2001 | Parodi |
| 6,280,545 | B1 * | 8/2001 | Kanesaka ......... A61M 25/1029 156/381 |
| 6,423,032 | B2 | 7/2002 | Parodi |
| 6,533,753 | B1 | 3/2003 | Haarstad et al. |
| 6,533,755 | B2 | 3/2003 | Adams |
| 6,942,640 | B2 | 9/2005 | Kokish |
| 7,314,364 | B2 | 1/2008 | Mahoney et al. |
| 8,257,382 | B2 | 9/2012 | Rottenberg et al. |
| 8,257,383 | B2 | 9/2012 | Rottenberg et al. |
| 2002/0068953 | A1 | 6/2002 | Kokish |
| 2010/0127436 | A1 | 5/2010 | Chen et al. |
| 2012/0165732 | A1 | 6/2012 | Muller |
| 2012/0265233 | A1 | 10/2012 | Waisman et al. |
| 2012/0323269 | A1 | 12/2012 | Rottenberg et al. |

FOREIGN PATENT DOCUMENTS

| | | |
|---|---|---|
| WO | 2011025855 A2 | 3/2011 |
| WO | 2011025855 A3 | 4/2011 |

\* cited by examiner

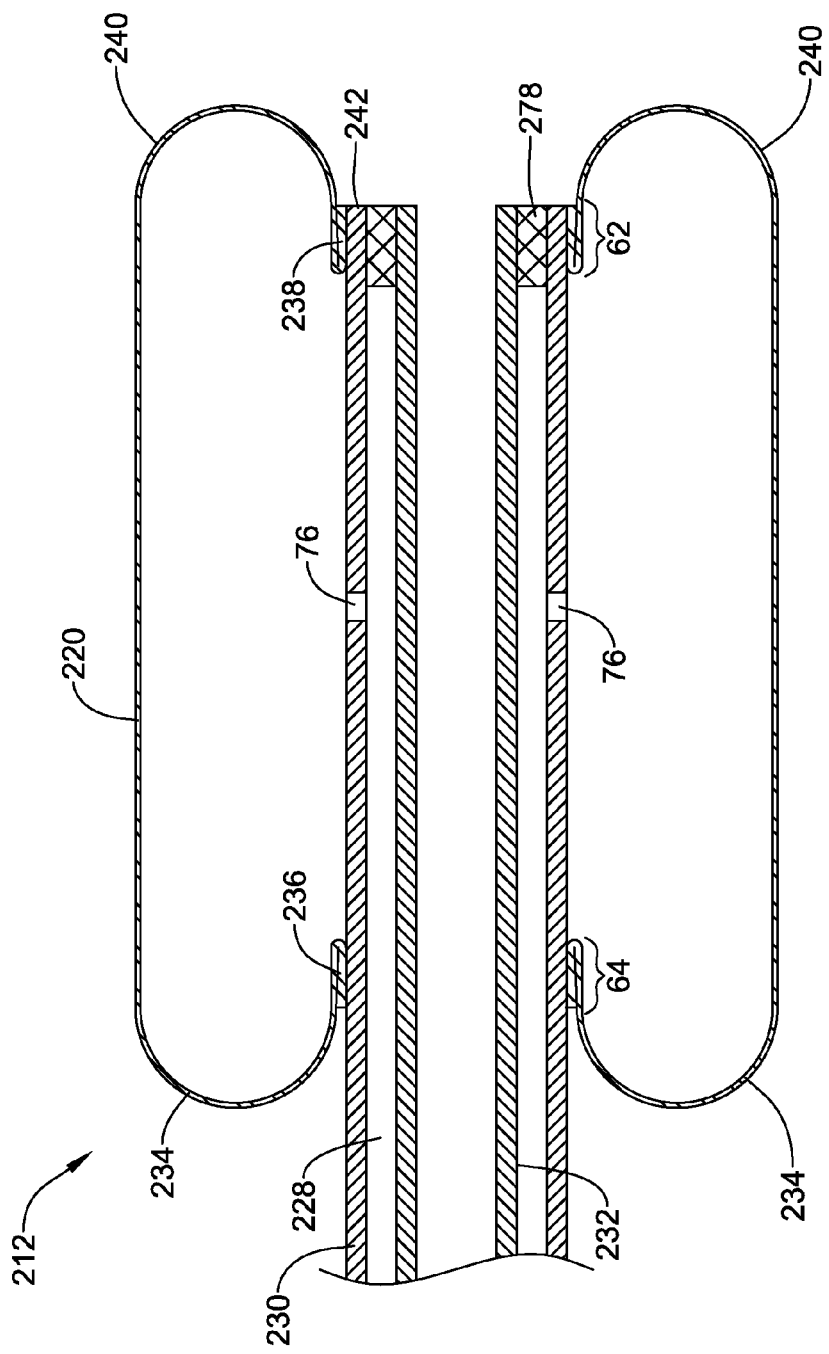

BALLOON CATHETER AND METHOD OF MANUFACTURE

CROSS-REFERENCES TO RELATED APPLICATIONS

The present application is a non-provisional of U.S. Provisional Application No. 61/885,270, filed Oct. 1, 2013, the complete disclosure of which is herein incorporated by reference.

TECHNICAL FIELD

The disclosure is directed to balloon catheters and the manufacture of balloon catheters. More particularly, the disclosure is directed to a method of manufacturing a balloon catheter including bonding the balloon parison to the catheter shaft prior to blow molding the balloon from the balloon parison. In some instances, the formed balloon may include an inverted balloon waist bonded to the catheter shaft. In other instances, the formed balloon may include one or more non-inverted balloon waists bonded to the catheter shaft.

BACKGROUND

A typical method for forming medical device balloons includes molding the balloon from a tubular balloon parison, such as an extruded tubular balloon parison, in a mold during a blow molding process. During the blow molding process, the mold is heated to elevate the temperature of the polymeric material (e.g., thermoplastic material) of the balloon parison in order to soften the polymeric material. While the balloon parison is at an elevated temperature, the interior of the balloon parison is pressurized to expand the softened polymeric material within the cavity of the mold such that the polymeric material conforms to the shape of the cavity to form the inflatable balloon. During a subsequent manufacturing process, the formed balloon is bonded to a catheter shaft to form the balloon catheter (e.g., the balloon waists are bonded to the catheter shaft after the balloon is blow molded).

Other medical device balloons are formed by dipping a balloon-shaped mandrel in a bath of liquid material or polymer. When dried, the liquid material or polymer forms a skin around the mandrel which can be removed and used as a balloon. For example, latex balloons are produced using this method.

In some instances, it may be difficult to secure a previously formed inflatable balloon to a catheter shaft during a subsequent balloon bonding process. For example, in some applications it may be desirable to provide the balloon catheter with no distal tip extending distal of the balloon. In such instances, the distal waist of the inflatable balloon may be inverted and bonded to the outer surface of the catheter shaft in an inverted orientation, thus positioning an inflatable portion of the balloon at or distal of the distal extremity of the catheter shaft. One such balloon catheter, configured for directing a re-entry device back into the true lumen during a subintimal recanalization procedure, is disclosed in U.S. Pat. No. 8,257,382, the disclosure of which is incorporated herein by reference. Other procedures in which a balloon catheter without a distal tip extending distal of the balloon may be advantageous include angioplasty, ablation, neuromodulation, kyphoplasty, and sinuplasty, for example. Inverting the balloon waist and/or securing the inverted balloon waist to the catheter shaft after the balloon blowing step is difficult and time consuming.

Accordingly, it is desirable to provide alternative methods of forming a balloon catheter and the resultant balloon catheter, such as a balloon catheter with an inflatable balloon having a proximal and/or distal inverted waist bonded to a component of the catheter shaft.

SUMMARY

The disclosure is directed to several alternative designs, materials and methods of manufacturing medical device structures and assemblies, and uses thereof.

Accordingly, one illustrative embodiment is a method of manufacturing a balloon catheter. The method includes attaching a distal end region of a tubular balloon parison to an outer surface of an elongate tubular member of a catheter shaft to form a distal bond region between the tubular balloon parison and the elongate tubular member of the catheter shaft. Alternatively, a proximal end region of the tubular balloon parison may be attached to the outer surface of the elongate tubular member of the catheter shaft to form a proximal bond region between the tubular balloon parison and the elongate tubular member of the catheter shaft. The tubular balloon parison and the elongate tubular member are positioned in a balloon mold with the bond region positioned in a cavity of the balloon mold. An annular space between an inner surface of the tubular balloon parison and the outer surface of the elongate tubular member is pressurized to expand the tubular balloon parison in the cavity of the balloon mold to form an inflatable balloon. The inflatable balloon and the elongate tubular member are removed from the balloon mold and a proximal waist of the inflatable balloon (or a distal waist of the inflatable balloon in embodiments in which a proximal bond region was formed prior to pressurizing the tubular balloon parison) is attached to the catheter shaft.

Another illustrative embodiment is a method of manufacturing a balloon catheter. The method includes extruding an elongate tubular member and a tubular balloon parison. The extruded elongate tubular member has an outer surface, an inner surface, and a length, and the extruded tubular balloon parison has an outer surface, an inner surface, and a length. The extruded tubular balloon parison is positioned around the extruded elongate tubular member and a distal end region of the extruded tubular balloon parison is secured to the outer surface of the extruded elongate tubular member to form a distal bond region between the extruded tubular balloon parison and the extruded elongate tubular member. The extruded tubular balloon parison and the extruded elongate tubular member are positioned in a balloon mold with the distal bond region positioned in a cavity of the balloon mold and a proximal end portion of the extruded tubular balloon parison extending proximally of the cavity of the balloon mold. An annular space between the inner surface of the extruded tubular balloon parison and the outer surface of the extruded elongate tubular member is pressurized to expand the extruded tubular balloon parison in the cavity of the balloon mold to form an inflatable balloon. The inflatable balloon and the extruded elongate tubular member are removed from the balloon mold and the proximal end portion of the extruded tubular balloon parison is removed after expanding the extruded tubular balloon parison to form the inflatable balloon. An outer tubular member is positioned over the elongate tubular member and a proximal waist of the inflatable balloon is secured to a distal end portion of the outer tubular member.

Yet another illustrative embodiment is a method of manufacturing a balloon catheter. The method includes bonding an inner surface of an extruded tubular balloon parison to an outer surface of an elongate tubular member of a catheter shaft to form a distal bond region between the extruded tubular balloon parison and the elongate tubular member of the catheter shaft. The extruded tubular balloon parison and the elongate tubular member are positioned in a balloon mold with the distal bond region positioned in a cavity of the balloon mold and a proximal portion of the extruded tubular balloon parison extending out of the balloon mold. An annular space between the inner surface of the extruded tubular balloon parison and the outer surface of the elongate tubular member is pressurized to expand the extruded tubular balloon parison in the cavity of the balloon mold to form an inflatable balloon. The inflatable balloon and the elongate tubular member are removed from the balloon mold and a proximal hub assembly is secured to a proximal end of the elongate tubular member.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIGS. 12-15 illustrate aspects of an alternative process of manufacturing a balloon catheter having a balloon with inverted proximal and distal balloon waists.

Figure 1:
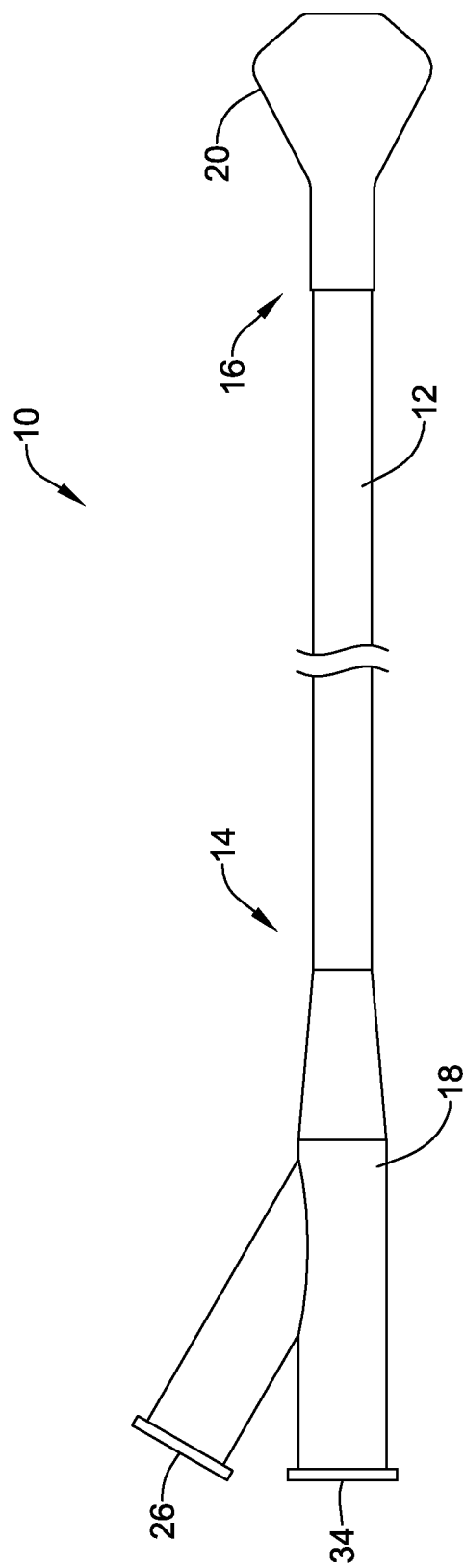
FIG. 1 is a plan view of an exemplary balloon catheter.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 2:
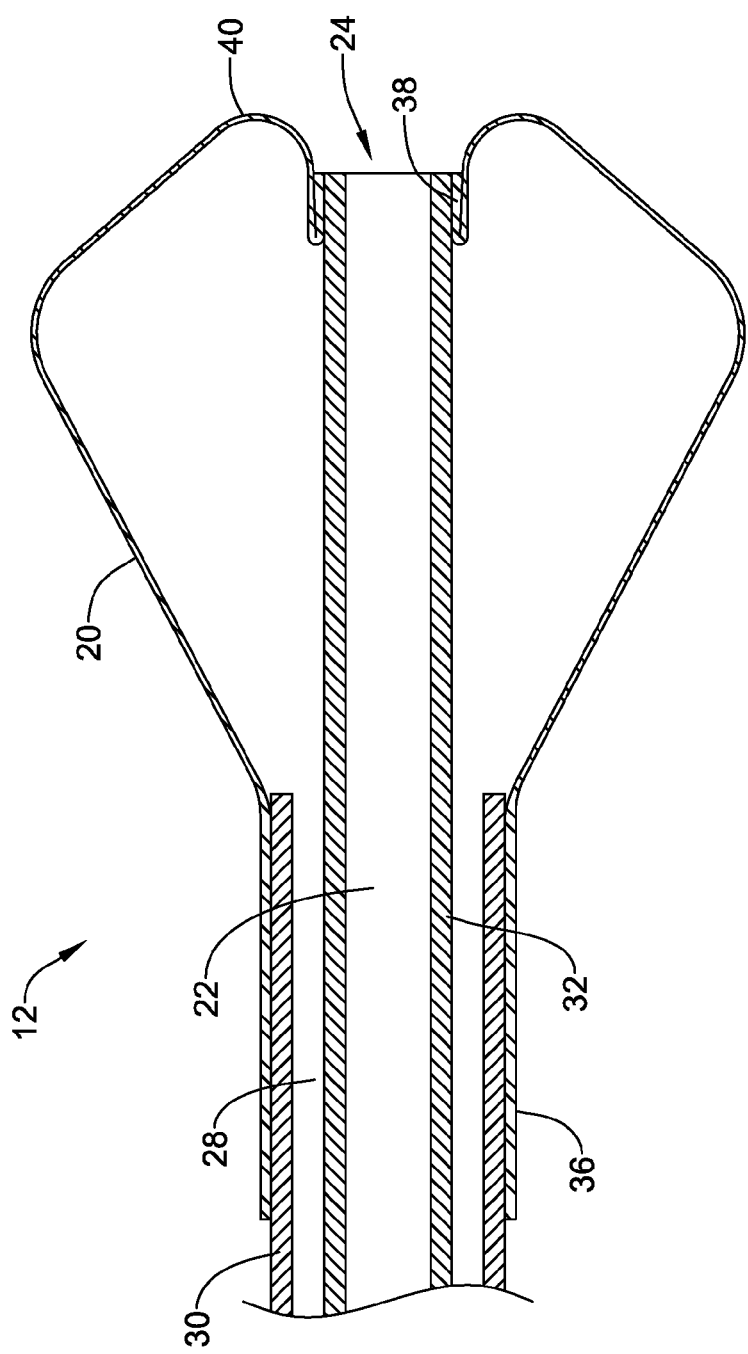
FIG. 2 is a longitudinal cross-sectional view of the distal end region of the balloon catheter of FIG. 1.

An exemplary balloon catheter is illustrated at FIG. 1, with a cross-sectional view of the distal end region of the balloon catheter illustrated at FIG. 2. The balloon catheter 10 may include a catheter shaft 12 extending distal from a hub assembly 18 mounted at a proximal end 14 of the catheter shaft to a distal end 16 of the catheter shaft 12. The balloon catheter 10 may include an inflatable balloon 20 mounted on a distal end region of the catheter shaft 12 proximal the distal end 16. It is noted that in other instances the inflatable balloon 20 may be mounted at a different location on the catheter shaft 12, if desired.

The catheter 10 may be configured to be advanced over a guidewire for delivery to a remote anatomical location, such as through the vasculature of a patient. For example, in some instances the catheter 10 may be configured as an over-the-wire (OTW) catheter having a guidewire lumen 22 (see FIG. 2) extending through the entire length of the catheter 10 from a distal port 24 at a distal tip of the catheter 10 to a proximal guidewire port 26 in the hub assembly 18. In other instances, the catheter 10 may be configured as a single-operator-exchange (SOE) catheter in which the guidewire lumen 22 may extend from the distal port 24 to a proximal guidewire port (not shown) located a short distance proximal of the inflatable balloon 20 and distal of the hub assembly 18. In such a configuration, a guidewire may extend through the guidewire lumen 22 between the distal port 24 and the proximal port, and extend along an exterior of the catheter shaft 12 proximal of the proximal port to the proximal end 14 of the catheter shaft 12. It is noted that in instances in which the catheter 10 is an SOE catheter, the hub assembly 18 may not include a proximal guidewire port 26. In other instances, the lumen 22 may be configured for another purpose, if desired.

Referring to FIG. 2, the catheter shaft 12 may include an outer tubular member 30 and an inner tubular member 32 extending through the outer tubular member 30. In some instances, the outer tubular member 30 may surround and/or be coaxially disposed with the inner tubular member 32. An inflation lumen 28 may be defined in the space between the outer surface of the inner tubular member 32 and the inner surface of the outer tubular member 30. The inflation lumen 28 may extend from and be in fluid communication with a proximal inflation port 34 to the inflatable balloon 20 at the distal end of the catheter shaft 12, such that inflation fluid may be passed through the inflation lumen 28 to inflate the inflatable balloon 20. In other embodiments, the catheter shaft 12 may include an extrude shaft component having a plurality of lumens formed therein, such as an extruded shaft component having a guidewire lumen and an inflation lumen formed therein. In such embodiments, a proximal waist and/or a distal waist of the balloon 20 may be attached to an outer surface of the extruded shaft component.

The outer tubular member 30 and/or the inner tubular member 32 may be an extruded tubular member formed during an extrusion process. In some instances, the outer tubular member 30 and/or the inner tubular member 32 may be a single layer extruded tube formed of a single layer of polymeric material. In other instances, the outer tubular member 30 and/or the inner tubular member 32 may be a multilayer extruded tube formed of multiple layers of polymeric materials. For example, the outer tubular member 30 and/or the inner tubular member 32 may include two, three, or more discrete layers of different polymer materials and/or compositions.

The balloon 20 may include a proximal waist 36 bonded, for example thermally bonded (e.g., laser, hot jaws) or adhesively bonded to a component of the catheter shaft 12. For example, the proximal waist 36 of the balloon 20 may be bonded or secured to the distal end of the outer tubular member 30. The balloon 20 may also include a distal waist 38 bonded, for example thermally bonded (e.g., laser, hot jaws) or adhesively bonded to a component of the catheter shaft 12. For example, the distal waist 38 of the balloon 20 may be bonded or secured to the distal end of the inner tubular member 32.

As shown in FIG. 2, the distal waist 38 may be inverted (e.g., extend proximally from the distal balloon tip 40) such that an inflatable portion of the balloon 20 is located at the distalmost extent of the catheter 10. Thus, the distal tip 40 of the balloon 20, which may be an inflatable portion of the balloon 20, may be positioned at or distal of the distal end of the inner tubular member 32 and distal of the distal waist 38 of the balloon 20.

Figure 3:
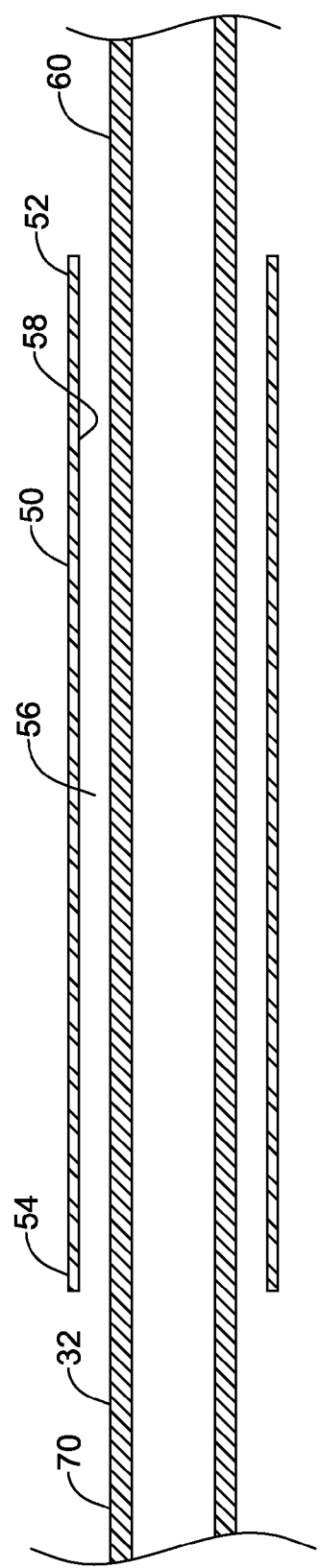
FIGS. 3-9 illustrate aspects of a process of manufacturing a balloon catheter having a balloon with an inverted distal balloon waist.

FIGS. 3-9 illustrate aspects of a process of manufacturing the balloon catheter 10 including the balloon 20 with an inverted distal balloon waist 38. As shown in FIG. 3, a tubular balloon parison 50 (i.e., a balloon preform) may be positioned over and surround a component of an elongate catheter shaft 70, such as an elongate tubular member of the catheter shaft 12 (e.g., the inner tubular member 32, the outer tubular member 30) such that the elongate tubular member 70 of the elongate catheter shaft (e.g., the inner tubular member 32, the outer tubular member 30) extends through the lumen 56 of the tubular balloon parison 50. It is noted that although the tubular balloon parison 50 is illustrated as being positioned over the inner tubular member 32, in other embodiments the tubular balloon parison 50 may be positioned over another elongate tubular member of the elongate catheter shaft, such as the outer tubular member 30, to be secured thereto.

The tubular balloon parison 50 may be an extruded tube formed during an extrusion process and then subsequently positioned over the component 70 of the elongate catheter shaft 12. The tubular balloon parison 50 may be a single layer extruded tube formed of a single layer of polymeric material. In other instances, the tubular balloon parison 50 may be a multilayer extruded tube formed of multiple layers of polymeric materials. For example, the tubular balloon parison 50 may include two, three, or more discrete layers of different polymer materials and/or compositions.

The tubular balloon parison 50 may have a first, distal end 52 and a second, proximal end 54, and a length measured from the first end 52 to the second end 54, with the lumen 56 extending through the tubular balloon parison 50 from the first, distal end 52 to the second, proximal end 54. In some instances, the tubular balloon parison 50 may be positioned around the component of the elongate catheter shaft (e.g., the inner tubular member 32, the outer tubular member 30) with distal end portion of the component of the elongate catheter shaft (e.g., the inner tubular member 32, the outer tubular member 30) extending distal of the first, distal end 52 and/or a proximal end portion of the component of the elongate catheter shaft (e.g., the inner tubular member 32, the outer tubular member 30) extending proximal of the second, proximal end 54.

Figure 4:
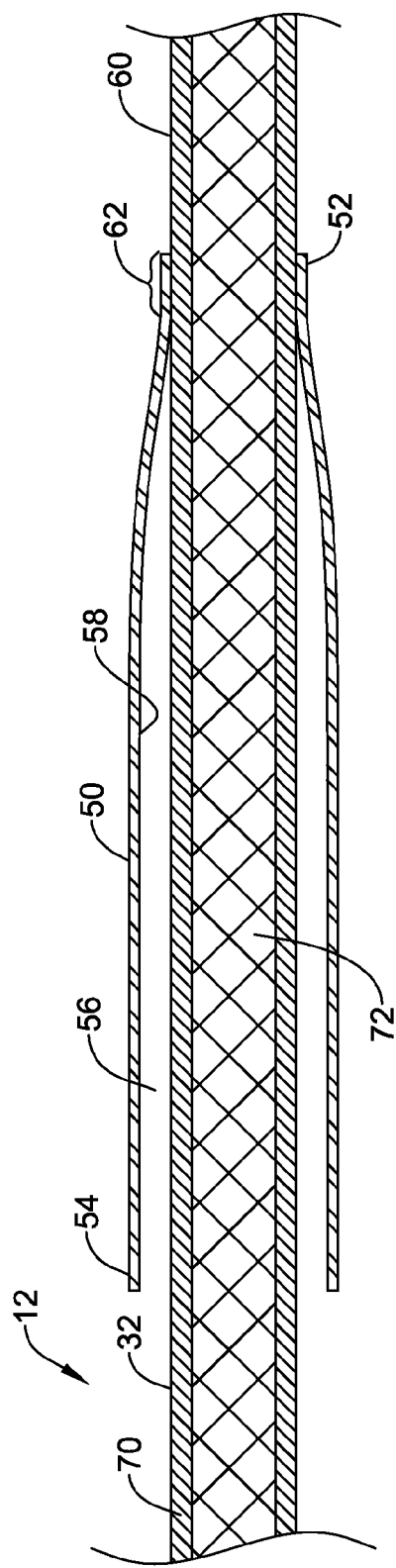

Turning to FIG. 4, the distal end region proximate the distal end 52 of the tubular balloon parison 50 may be secured to the elongate tubular member 70 of the catheter shaft 12 at a distal bonding region using a desired bonding technique. For example, an inner surface 58 of the distal end region of the tubular balloon parison 50 may be thermally bonded (e.g., laser bonded, hot jaws, etc.) or adhesively bonded to the outer surface 60 of the tubular catheter shaft component 70 to form a distal bond region 62 between the tubular balloon parison 50 and the elongate tubular member of the catheter shaft. In some instances, the distal end region of the tubular balloon parison 50 may be reduced in diameter to be bonded to the elongate catheter shaft component 70, while the remainder of the tubular balloon parison 50 may have an inner diameter larger than the outer diameter of the elongate catheter shaft component 70, such that the inner surface 58 of the tubular balloon parison 50 is spaced away from the outer surface 60 of the elongate catheter shaft component 70.

Figure 5:
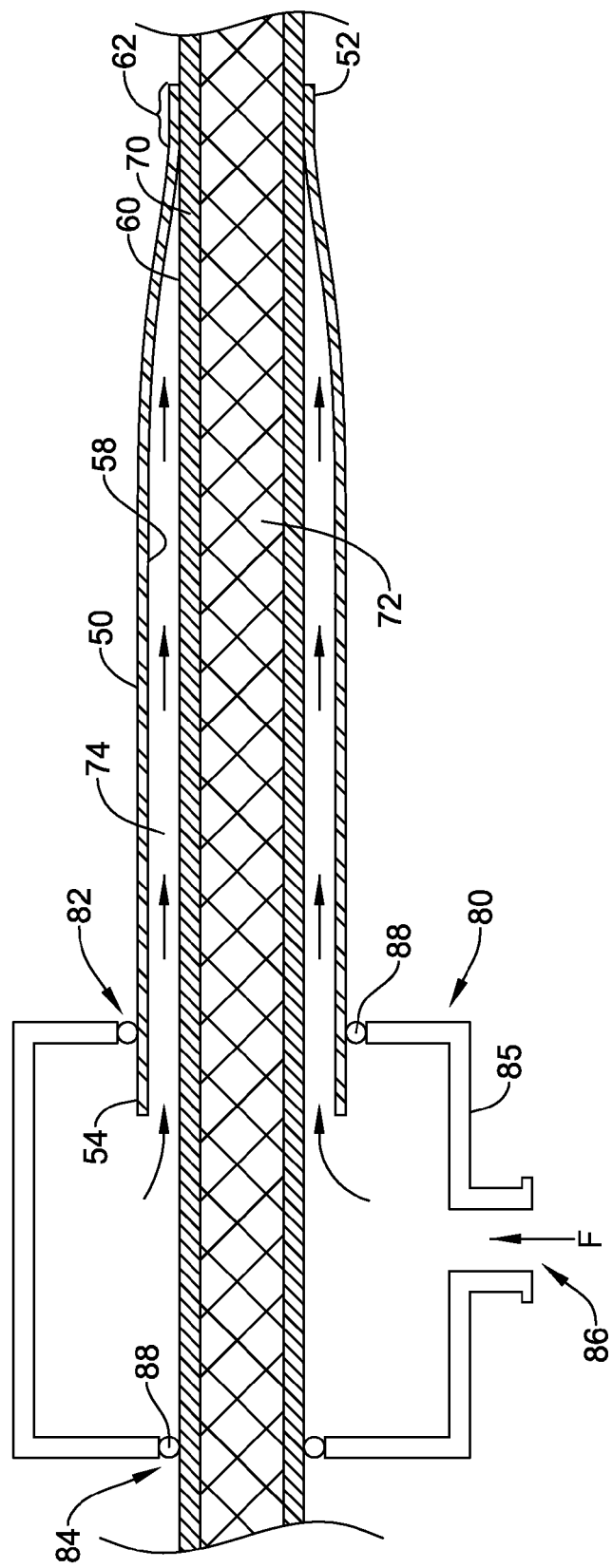

The elongate catheter shaft component 70 and the tubular balloon parison 50 may be attached to a pressurization fixture 80, as shown in FIG. 5, configured to supply fluid pressure between the tubular balloon parison 50 and the elongate catheter shaft component 70 to expand and stretch the tubular balloon parison 50. A mandrel 72 may also be inserted into the lumen of the tubular catheter shaft component 70 to provide support and alignment of the assembly, as well as maintain the lumen of the catheter shaft component 70 during subsequent manufacturing processes (e.g., prevent the catheter shaft component 70 from collapsing during the subsequent balloon blow molding step described herein.

The pressurization fixture 80 may include a housing 85 having a coupling portion 82 configured to sealingly couple to the tubular balloon parison 50 and a coupling portion 84 configured to sealingly couple to the tubular catheter shaft component 70. For instance, the pressurization fixture 80 may include a seal 88 sealingly surrounding a proximal end portion of the tubular balloon parison 50 and a seal 88 sealingly surrounding the tubular catheter shaft component 70. The pressurization fixture 80 may also include a fluid inlet 86 to supply pressurization fluid F into the pressurization fixture 80. The pressurization fixture 80 may be configured to direct the pressurized fluid F between the outer surface 60 of the tubular catheter shaft component 70 and the inner surface 58 of the tubular balloon parison 50. For example, the pressurization fixture 80 may be configured to direct the pressurized fluid F into an annular space 74 between the tubular catheter shaft component 70 and the tubular balloon parison 50. It is noted that in other instances the pressurization fixture 80 may be structured and/or arranged in other manners to direct pressurization fluid between the tubular balloon parison 50 and the tubular catheter shaft component 70.

Figure 6:
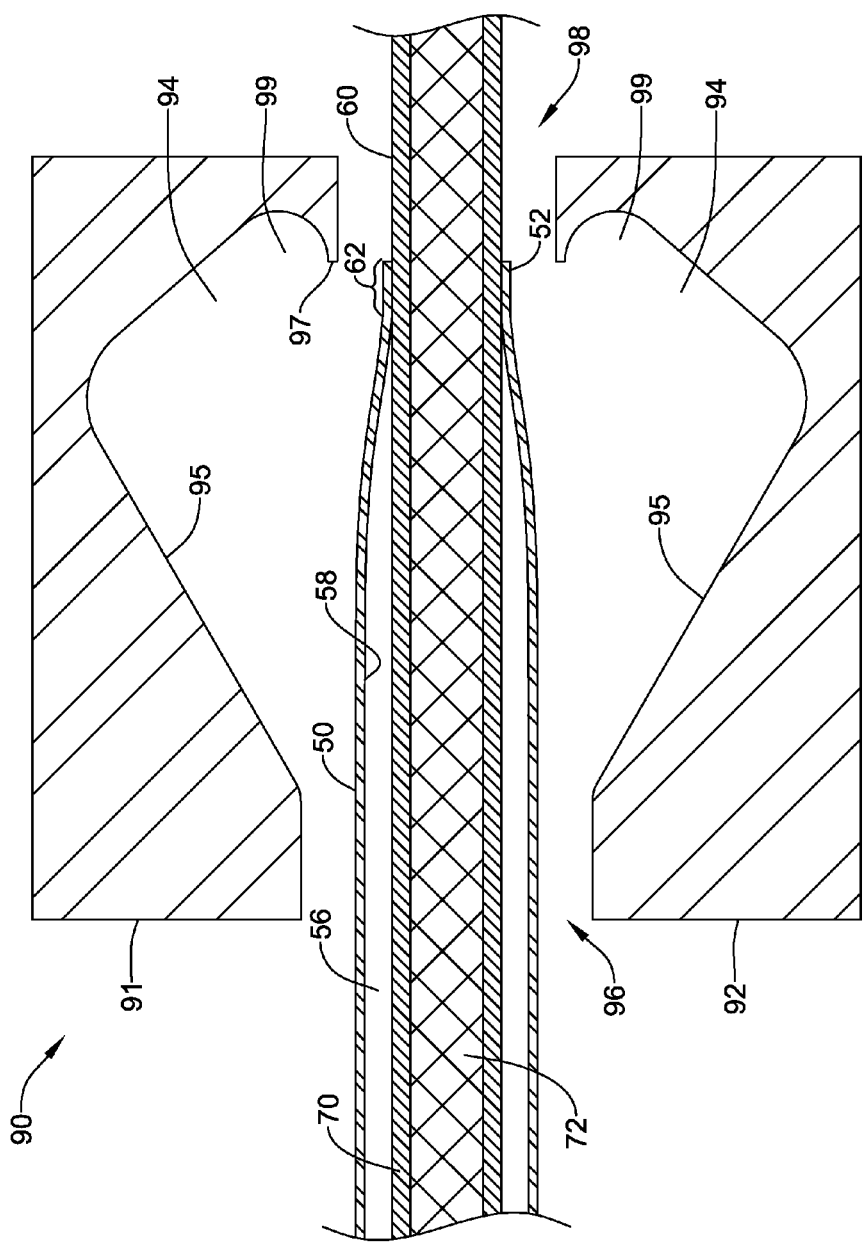
Figure 7:
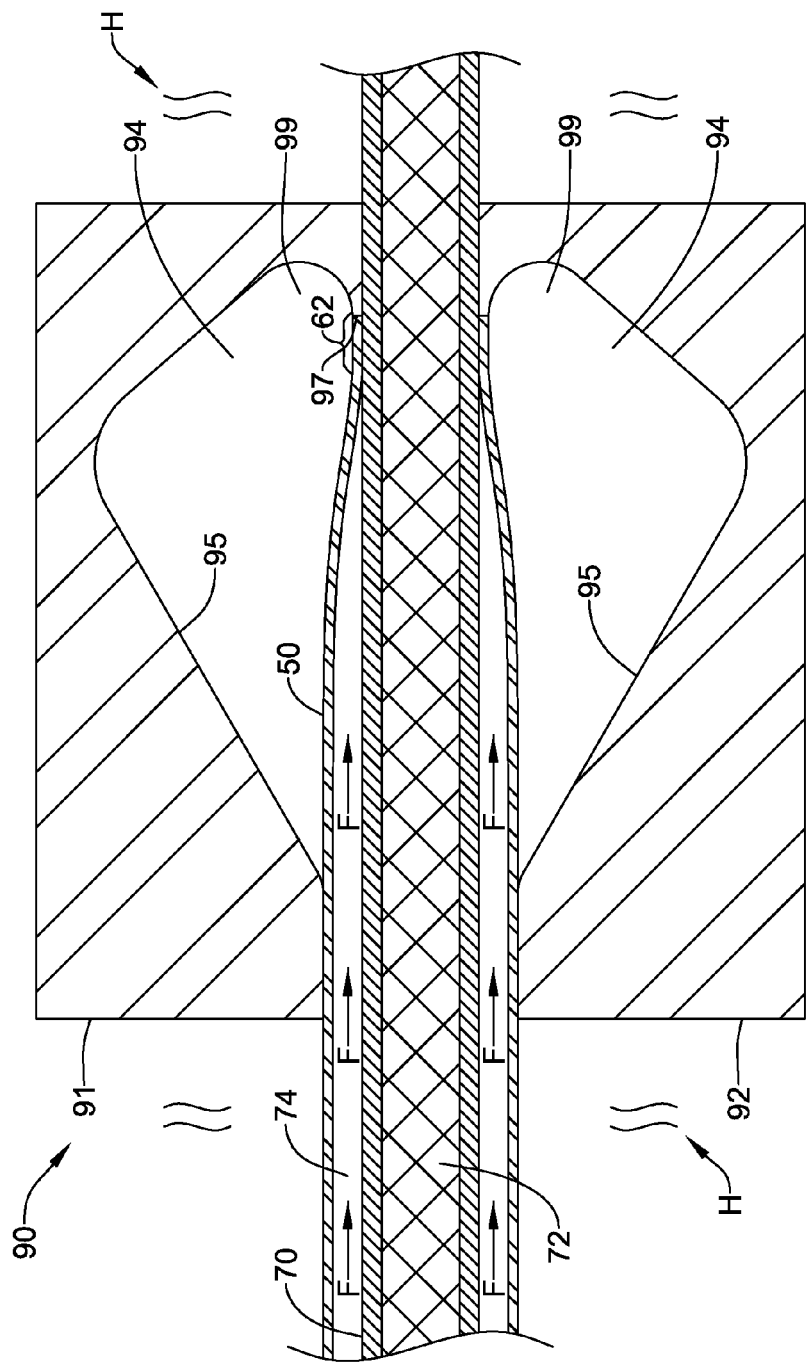

The tubular balloon parison 50 and the tubular catheter shaft component 70 may be positioned in a balloon mold 90 with the distal bond region 62 positioned in a cavity 94 of the balloon mold 90, as shown in FIG. 6. In some instances, the balloon mold 90 may be formed of multiple components, such as a first mold component 91 and a second mold component 92, although in some instances the balloon mold 90 may include additional mold components. In some instances, the first mold component 91 may form a first half of the balloon mold 90 and the second mold component 92 may form a second half of the balloon mold 90. The tubular balloon parison 50 and the tubular catheter shaft component 70 may be positioned in the balloon mold 90 with the balloon mold 90 in an open state, as shown in FIG. 6, and subsequently the balloon mold 90 may be closed around the tubular balloon parison 50 and the tubular catheter shaft component 70, as shown in FIG. 7.

In some embodiments, the balloon mold 90 may include a first opening 96 at a first end of the balloon mold 90 sized to permit a proximal portion of the tubular balloon parison 50 and the tubular catheter shaft component 70 to extend proximally therefrom and provide support for the assembly in the balloon mold 90. The first opening 96 may have a diameter approximately equal to the outer diameter of the tubular balloon parison 50 such that the balloon mold 90 closely fits around the tubular balloon parison 50 at the first opening 96.

In some embodiments, the balloon mold 90 may include a second opening 98 at a second end of the balloon mold 90 sized to permit a distal portion of the tubular catheter shaft component 70 to extend distally therefrom and provide support for the assembly in the balloon mold 90. The second opening 98 may have a diameter approximately equal to the outer diameter of the tubular catheter shaft component 70 such that the balloon mold 90 closely fits around the tubular catheter shaft component 70 at the second opening 98.

The cavity 94 within the balloon mold 90, defined by an inner surface 95 of the balloon mold 90, may be configured to the size and shape of the desired size and shape of the balloon to be formed from the tubular balloon parison 50 within the balloon mold 90 during the blow molding process. For example, as shown in FIG. 6, in some instances, the cavity 94 may be conically shaped to form a generally conically shaped balloon. The balloon mold 90 may include a rim 97 configured to be positioned distal of the distal bond region 62, with a portion 99 of the cavity 94 extending distal of the rim 97. In some instances, the distal bond region 62 may be juxtaposed with the rim 97 when positioned in the cavity 94 of the balloon mold 90. The portion 99 of the cavity 94 extending distally of the distal bond region 62 and the rim 97 may be an annular portion configured to form an inflatable distal tip portion of the balloon.

The balloon mold 90 may be closed around the tubular balloon parison 50 and the tubular catheter shaft component 70, as shown in FIG. 7, and the tubular balloon parison 50 may be heated (shown by reference H) to an elevated temperature to soften the polymeric material of the tubular balloon parison 50 to permit the tubular balloon parison 50 to be stretched during the balloon blow molding process. For instance, the balloon mold 90 may be heated to an elevated temperature to heat the tubular balloon parison 50. In some embodiments, the balloon mold 90, with the tubular balloon parison 50 and the tubular catheter shaft component 70 positioned therein, may be placed in a heated liquid bath, or other heated chamber, to heat the tubular balloon parison 50 to an elevated temperature to soften the polymeric material of the tubular balloon parison 50 for the blow molding/stretching process. In other instances, heat may be applied by different means, such as induction heating, steam, hot air, etc.

With the tubular balloon parison 50 heated to an elevated temperature and softened, the annular space 74 between the tubular balloon parison 50 and the tubular catheter shaft component 70 may be pressurized with a fluid F to expand and stretch the tubular balloon parison 50 in the cavity 94 of the balloon mold 90 to form an inflatable balloon. The fluid F may be directed to the annular space 74 using the pressurization fixture 80 shown in FIG. 5, or other pressurization fixture.

Figure 8:
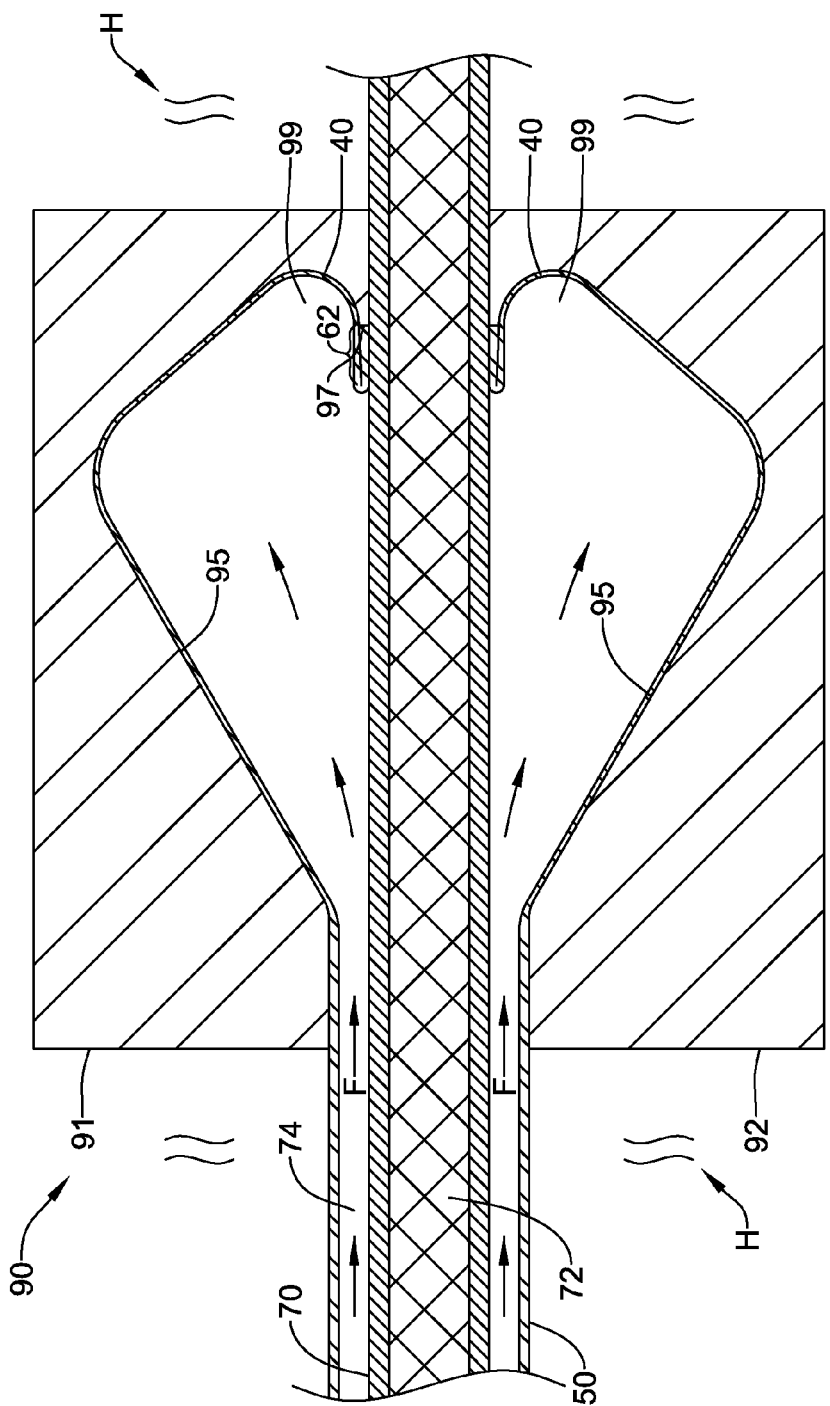

As shown in FIG. 8, the tubular balloon parison 50 may be expanded and stretched to conform to the inner surface 95 of the cavity 94 of the balloon mold 90. As the tubular balloon parison 50 is expanded and stretched, the thickness of the tubular balloon parison 50 is reduced to create a pliable inflatable balloon from the tubular balloon parison 50. A portion of the tubular balloon parison 50 may stretch and expand distally of the distal bond region 62 to conform with the portion 99 of the cavity 94 distal of the rim 97 and distal bond region 62 to form an inflatable distal portion 40, such as an inflatable distal tip portion, of the balloon 20.

Figure 9:
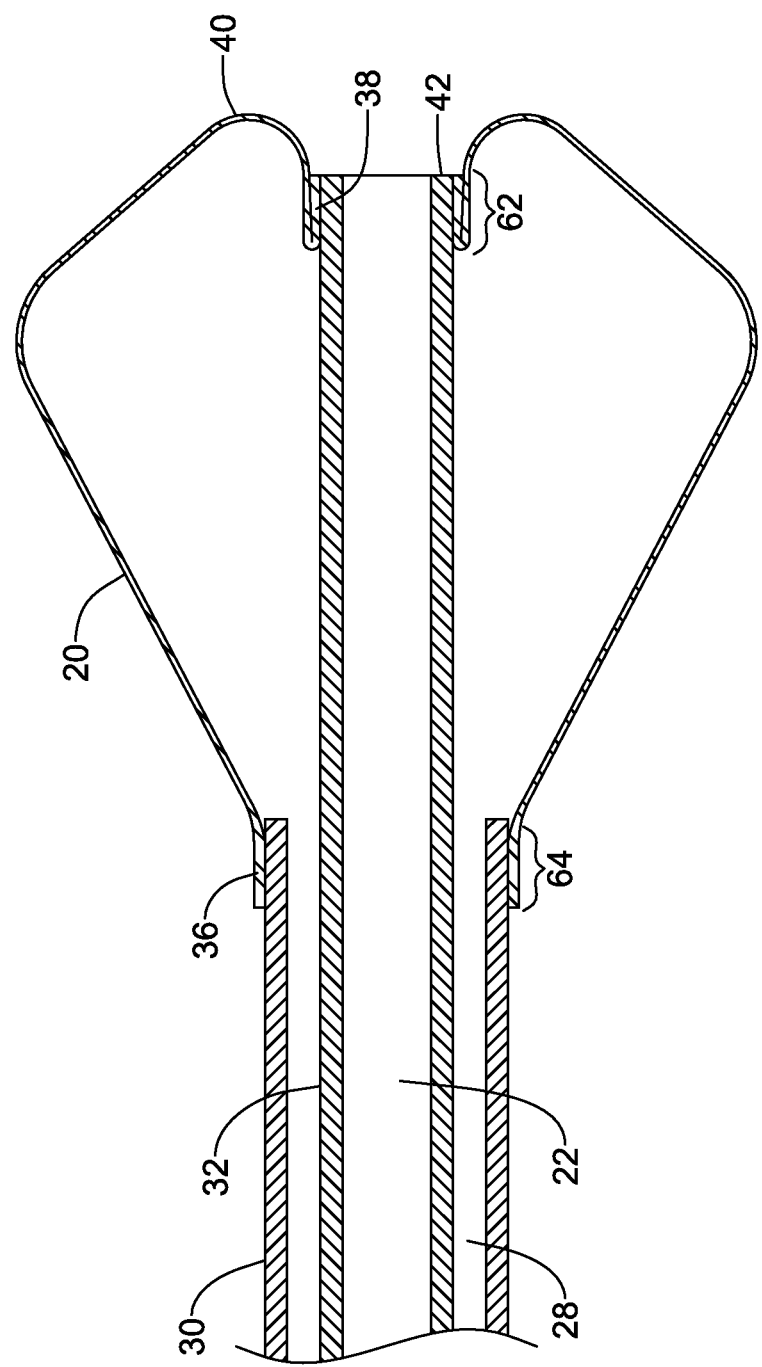

Once the blow molding process is complete and the tubular balloon parison 50 has been blown and stretched to conform to the cavity 94 to form the balloon 20, the assembly may then be removed from the balloon mold 90. As shown in FIG. 9, the assembly, with the blown balloon 20 bonded to the catheter shaft component 70 may be used in a catheter assembly with the catheter shaft component 70 used as an inner tubular member 32 of the catheter shaft 12. As shown in FIG. 9, a distal portion of the tubular catheter shaft component 70 (e.g., the inner tubular member 32) may be removed (e.g., cut off) such that a distal end 42 of the tubular catheter shaft component 70 (e.g., the inner tubular member 32) is located at or proximal of the inflatable distal tip portion 40 of the balloon 20. Thus, the distal waist 38, formed by the distal bond region 62, may be an inverted distal waist extending proximally into the interior of the balloon 20 from a distal extent of the balloon 20, such that the inflatable distal tip portion 40 of the balloon 20 is the distalmost extent of the balloon 20. In other embodiments a distal portion of the tubular catheter shaft component 70 may be retained, providing a distal tip region extending distal of the distalmost extent of the balloon 20. In some instances, a distal tip may be attached to the tubular catheter shaft component 70 and extend distally therefrom. For example, the distal tip may extend distal of the balloon 20 in some instances.

Additionally, a proximal portion of the tubular balloon parison 50 remaining after blow molding the balloon 20 therefrom, may be removed (e.g., cut off) and a proximal waist 36 of the balloon 20 may be secured or bonded (e.g., thermally or adhesively bonded) to a catheter shaft component. For example, an outer tubular member 30 may be positioned over the inner tubular member 32 such that the proximal balloon waist 36 may be secured to the distal end of the outer tubular member 30 at a proximal bond region 64. Thus, the balloon 20 may be sealingly affixed to the catheter shaft such that the interior of the balloon 20 is in fluid communication with the inflation lumen 28.

Furthermore, the inner tubular member 32 and/or the outer tubular member 30 may be attached (e.g., bonded) to the hub assembly 18 (shown in FIG. 1) such that the inflation lumen 28 is in fluid communication with the inflation port 34 and the guidewire lumen 22 is in communication with the guidewire port 26.

In other instances, the above described process may be implemented to form a proximal waist, such as an inverted proximal waist, bonded to a balloon prior to blow molding the balloon with the balloon parison bonded to the catheter shaft component prior to the blow molding step. For instance, reference to "proximal" and "distal" in describing various components, regions, and directions may be substituted with "distal" and "proximal", respectively, in describing such a process and resultant structure to the extent that such substitution is logical. For example, one exemplary method may include attaching a first, proximal end region of a tubular balloon parison to an outer surface of an elongate tubular member of a catheter shaft to form a first, proximal bond region between the tubular balloon parison and the elongate tubular member of the catheter shaft. The tubular balloon parison and the elongate tubular member may then be positioned in a balloon mold with the proximal bond region positioned in a cavity of the balloon mold. An annular space between an inner surface of the tubular balloon parison and the outer surface of the elongate tubular member may then be pressurized to expand the tubular balloon parison in the cavity of the balloon mold to form an inflatable balloon. The inflatable balloon and the elongate tubular member may then be removed from the balloon mold and a distal waist of the inflatable balloon may be attached to the catheter shaft. The first, proximal end region of the tubular balloon parison may form a proximal waist, such as an inverted proximal waist, of the inflatable balloon attached to the elongate tubular member.

Figure 10:
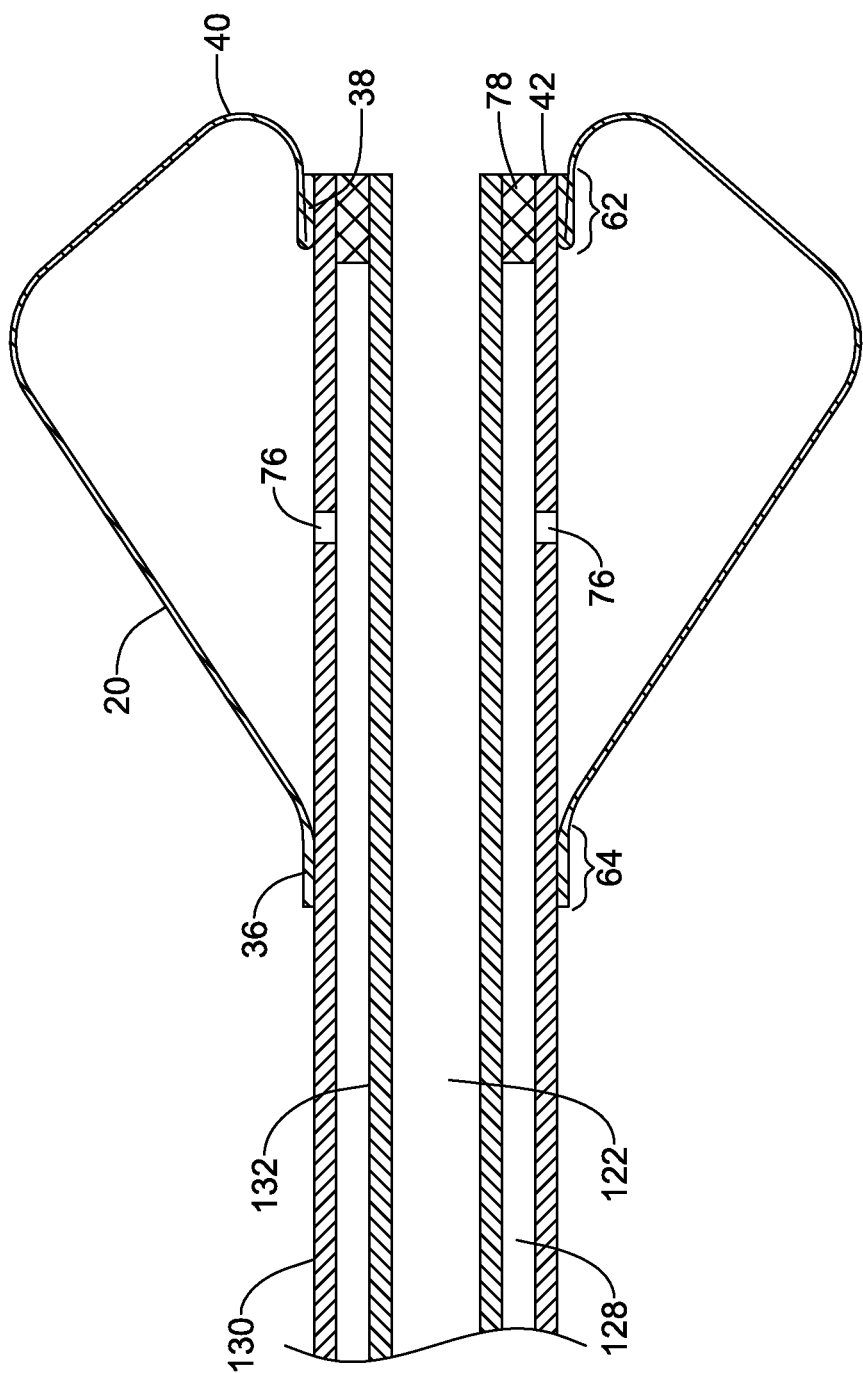
FIG. 10 is an alternative configuration of a balloon catheter formed in accordance with the manufacturing processes of FIGS. 3-8.

In another embodiment, as shown in FIG. 10, the assembly, with the blown balloon 20 bonded to the catheter shaft component 70 may be used in a catheter assembly with the catheter shaft component 70 used as an outer tubular member 130 of the catheter shaft. As shown in FIG. 10, a distal portion of the tubular catheter shaft component 70 (e.g., the outer tubular member 130) may be removed (e.g., cut off) such that a distal end 42 of the tubular catheter shaft component 70 (e.g., the outer tubular member 130) is located at or proximal of the inflatable distal tip portion 40 of the balloon 20. Thus, the distal waist 38, formed by the distal bond region 62, may be an inverted distal waist extending proximally into the interior of the balloon 20 from a distal extent of the balloon 20, such that the inflatable distal tip portion 40 of the balloon 20 is the distalmost extent of the balloon 20.

Additionally, a proximal portion of the tubular balloon parison 50 remaining after blow molding the balloon 20 therefrom, may be removed (e.g., cut off) and a proximal waist 36 of the balloon 20 may be secured or bonded (e.g., thermally or adhesively bonded) to a catheter shaft component. For example, the proximal balloon waist 36 may be secured to the outer tubular member 130 at a proximal bond region 64.

An inner tubular member 132, defining a guidewire lumen 122, may be positioned within the outer tubular member 130 and an inflation lumen 128 may be defined between the inner tubular member 132 and the outer tubular member 130. The inner tubular member 132 may be bonded (e.g., thermally or adhesively bonded) to the outer tubular member 130 at a bond region 78 proximate the distal ends of the inner tubular member 132 and the outer tubular member 130. The outer tubular member 130 may include one or more, or a plurality of openings 76 permitting fluid to pass from the inflation lumen 128 into the interior of the balloon 20. Thus, the balloon 20 may be sealingly affixed to the catheter shaft such that the interior of the balloon 20 is in fluid communication with the inflation lumen 128.

Furthermore, the inner tubular member 132 and/or the outer tubular member 130 may be attached (e.g., bonded) to a hub assembly having an inflation port in fluid communication with the inflation lumen 128 and/or a guidewire port in communication with the guidewire lumen 122.

Figure 11:
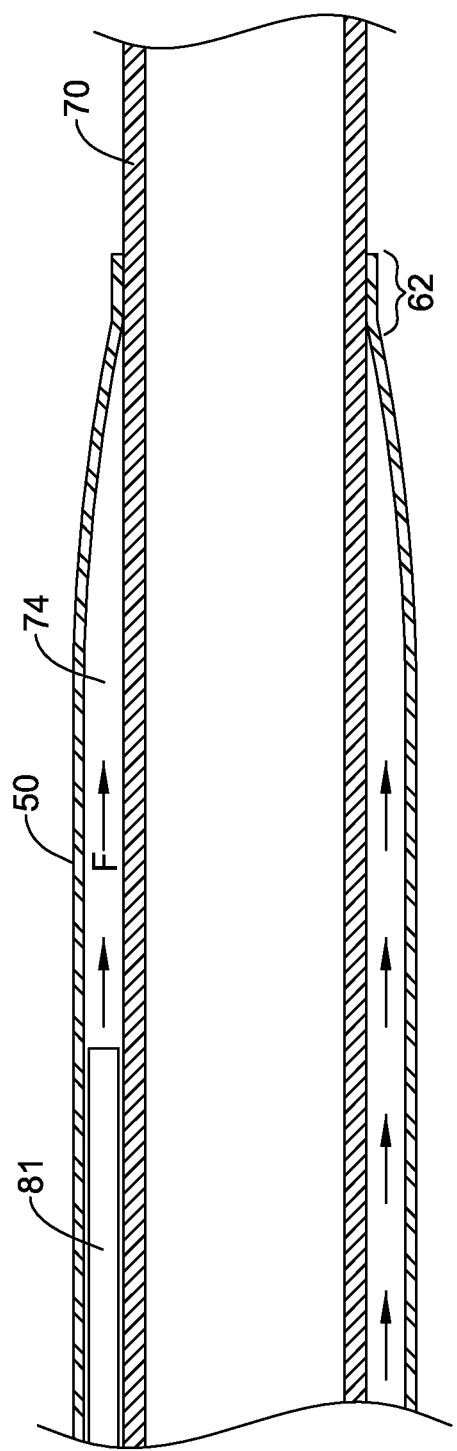
FIG. 11 is an alternative configuration of pressurizing the interior of a balloon parison secured to a catheter shaft during a manufacturing process in accordance with the disclosure.

In an alternative embodiment, shown in FIG. 11, the pressurization fixture 80 used to provide a pressurization fluid F into the annular space 74 between the tubular catheter shaft component 70 and the tubular balloon parison 50 may include a structure configured to be positioned in the annular space 74 to maintain a passageway for delivering the pressurization fluid F into the annular space 74. For example, an elongated tube 81, such as a metallic hypotube, or other rigid tubular member, may be inserted into the annular space 74 to permit pressurization fluid F to be delivered through the elongated tube 81 into the annular space 74 during the balloon blowing process.

Figure 12:
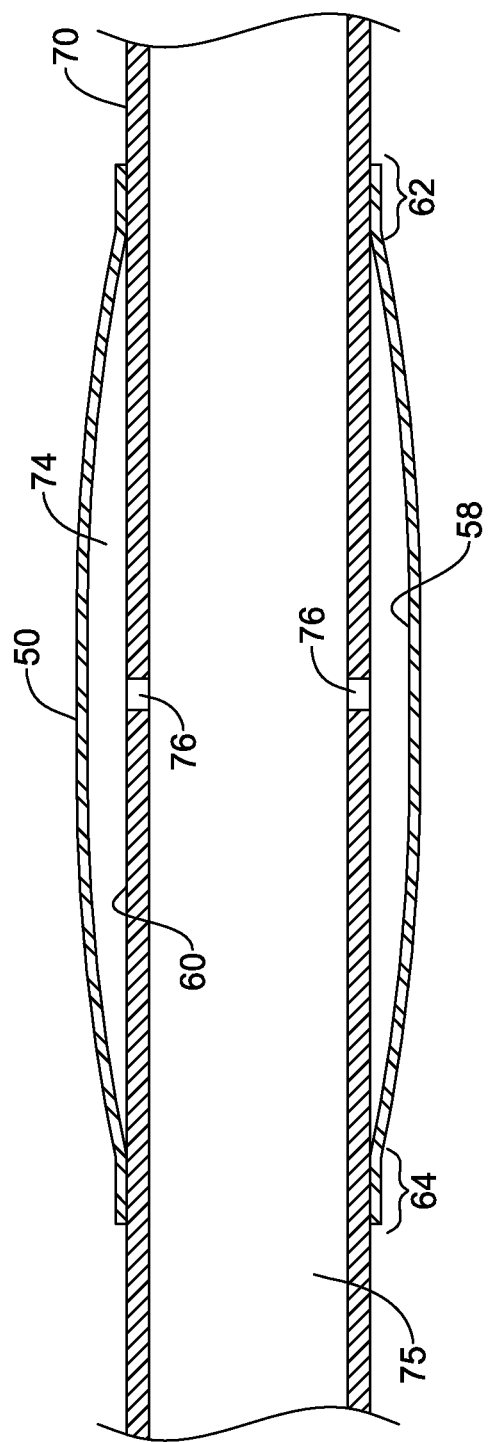

FIGS. 12-15 illustrate aspects of an alternative process of manufacturing a balloon catheter having a tubular balloon parison 50 bonded to a catheter shaft component 70 prior to blow molding a balloon from the tubular balloon parison 50. As shown in FIG. 12, a tubular balloon parison 50 (i.e., a balloon preform) may be positioned over and surround a component of an elongate catheter shaft 70, such that the elongate tubular member 70 of the elongate catheter shaft extends through the tubular balloon parison 50. The tubular balloon parison 50 may be an extruded tube (e.g., single layer or multilayer extruded tube) formed during an extrusion process and then subsequently positioned over the component 70 of the elongate catheter shaft 12.

A first region of the tubular balloon parison 50, such as a distal end region proximate the distal end of the tubular balloon parison 50, may be secured to the elongate tubular catheter shaft component 70 at a distal bonding region 62 using a desired bonding technique. A second region of the tubular balloon parison 50, such as a proximal end region proximate the proximal end of the tubular balloon parison 50, may be secured to the elongate tubular catheter shaft component 70 at a proximal bonding region 64 using a desired bonding technique. Any desired bonding technique may be used, such as a thermal or adhesive bonding technique.

In some instances, the proximal end region and/or the distal end region of the tubular balloon parison 50 may be reduced in diameter to be bonded to the elongate catheter shaft component 70, while the remainder of the tubular balloon parison 50 may have an inner diameter larger than the outer diameter of the elongate catheter shaft component 70, such that the inner surface 58 of the tubular balloon parison 50 is spaced away from the outer surface 60 of the elongate catheter shaft component 70 to define an annular space 74 therebetween. In some instances, a mandrel may be placed through the elongate catheter shaft component 70 while the proximal end region and/or the distal end region of the tubular balloon parison 50 is bonded to the elongate catheter shaft component 70. The elongate catheter shaft component 70 may include one or more, or a plurality of openings 76 positioned at a location between the proximal and distal bond regions 64, 62 permitting fluid to pass from the lumen 75 of the catheter shaft component into the annular space 74.

A distal portion of the catheter shaft component 70 may be sealed off to prevent pressurized fluid from exiting the lumen 75 at the distal end of the catheter shaft component

70. For example, a seal 260, shown in FIG. 13, may be positioned at the distal end of the elongate catheter shaft component 70 to close off or seal the lumen 75. In other instances, the wall of the catheter shaft component 70 proximate the distal end of the catheter shaft component 70 may be collapsed to seal the lumen 75. The elongate catheter shaft component 70 and the tubular balloon parison 50 may be attached to a pressurization fixture (not shown) configured to supply fluid pressure through the lumen 75 of the elongate catheter shaft component 70 and into the annular space 74 through the opening(s) 76 to expand and stretch the tubular balloon parison 50.

Figure 13:
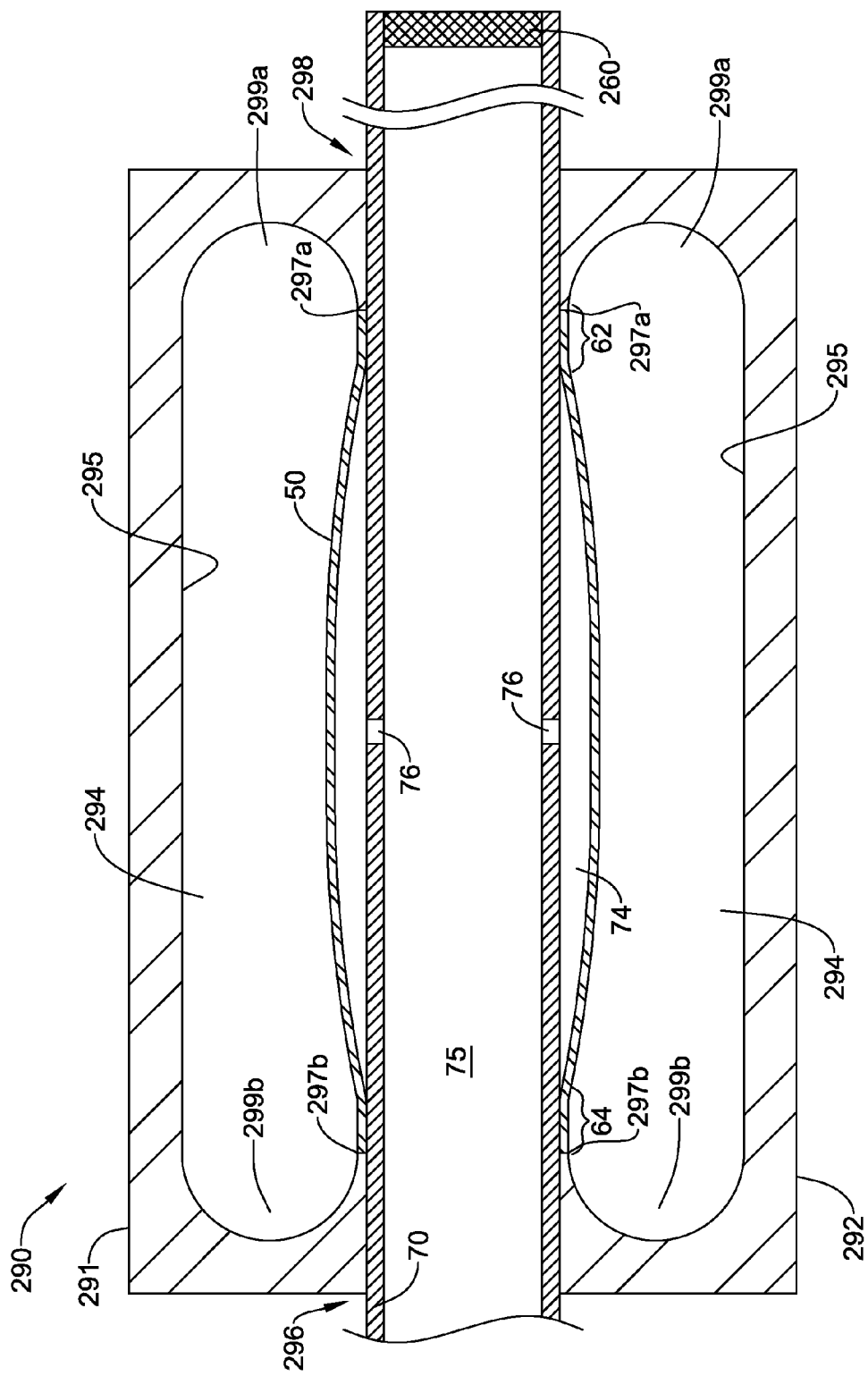

As shown in FIG. 13, the tubular balloon parison 50 and the tubular catheter shaft component 70 may be positioned in a balloon mold 290 with the distal bond region 62 positioned in a cavity 294 of the balloon mold 290 proximal of a distal rim 297*a* and the proximal bond region 64 positioned in the cavity 94 of the balloon mold 290 distal of a proximal rim 297*b*. In some instances, the balloon mold 290 may be formed of multiple components, such as a first mold component 291 and a second mold component 292, although in some instances the balloon mold 290 may include additional mold components. In some instances, the first mold component 291 may form a first half of the balloon mold 290 and the second mold component 292 may form a second half of the balloon mold 290. The tubular balloon parison 50 and the tubular catheter shaft component 70 may be positioned in the balloon mold 290 with the balloon mold 290 in an open state and subsequently the balloon mold 290 may be closed around the tubular balloon parison 50 and the tubular catheter shaft component 70, as shown in FIG. 13.

In some embodiments, the balloon mold 290 may include a first opening 296 at a first end of the balloon mold 290 sized to permit a proximal portion of the tubular catheter shaft component 70 to extend proximally therefrom and provide support for the assembly in the balloon mold 290 and/or the balloon mold 290 may include a second opening 298 at a second end of the balloon mold 290 sized to permit a distal portion of the tubular catheter shaft component 70 to extend distally therefrom and provide support for the assembly in the balloon mold 290. The first opening 296 and/or the second opening 298 may have a diameter approximately equal to the outer diameter of the tubular catheter shaft component 70 such that the balloon mold 90 closely fits around the tubular catheter shaft component 70 at the first opening 296 and/or second opening 298. The tubular balloon parison 50 and the tubular catheter shaft component 70 may be positioned in the balloon mold 290 such that the entire length of the tubular balloon parison 50 (i.e., the length between the proximal and distal ends of the tubular balloon parison 50) is positioned in the cavity 294, such as positioned entirely between the proximal and distal rims 297*b*, 297*a* of the cavity 294.

The cavity 294 within the balloon mold 290, defined by an inner surface 295 of the balloon mold 290, may be configured to the size and shape of the desired size and shape of the balloon to be formed from the tubular balloon parison 50 within the balloon mold 290 during the blow molding process. For example, as shown in FIG. 13, in some instances, the cavity 294 may be generally cylindrically shaped to form a generally cylindrically shaped balloon. The balloon mold 290 may include distal portion 299*a* extending distal of the distal rim 297*a* and a proximal portion 299*b* extending proximal of the proximal rim 297*b*, with the distal rim 297*a* configured to be positioned distal of the distal bond region 62 and the proximal rim 297*b* configured to be positioned proximal of the proximal bond region 64. In some instances, the distal bond region 62 may be juxtaposed with the distal rim 297*a* and/or the proximal bond region 64 may be juxtaposed with the proximal rim 297*b* when positioned in the cavity 294 of the balloon mold 290. The portion 299*a* of the cavity 294 extending distally of the distal bond region 62 and the rim 297*a* may be an annular portion configured to form an inflatable distal end portion of the balloon and the portion 299*b* of the cavity 294 extending proximally of the proximal bond region 64 and the rim 297*b* may be an annular portion configured to form an inflatable proximal end portion of the balloon.

Figure 14:
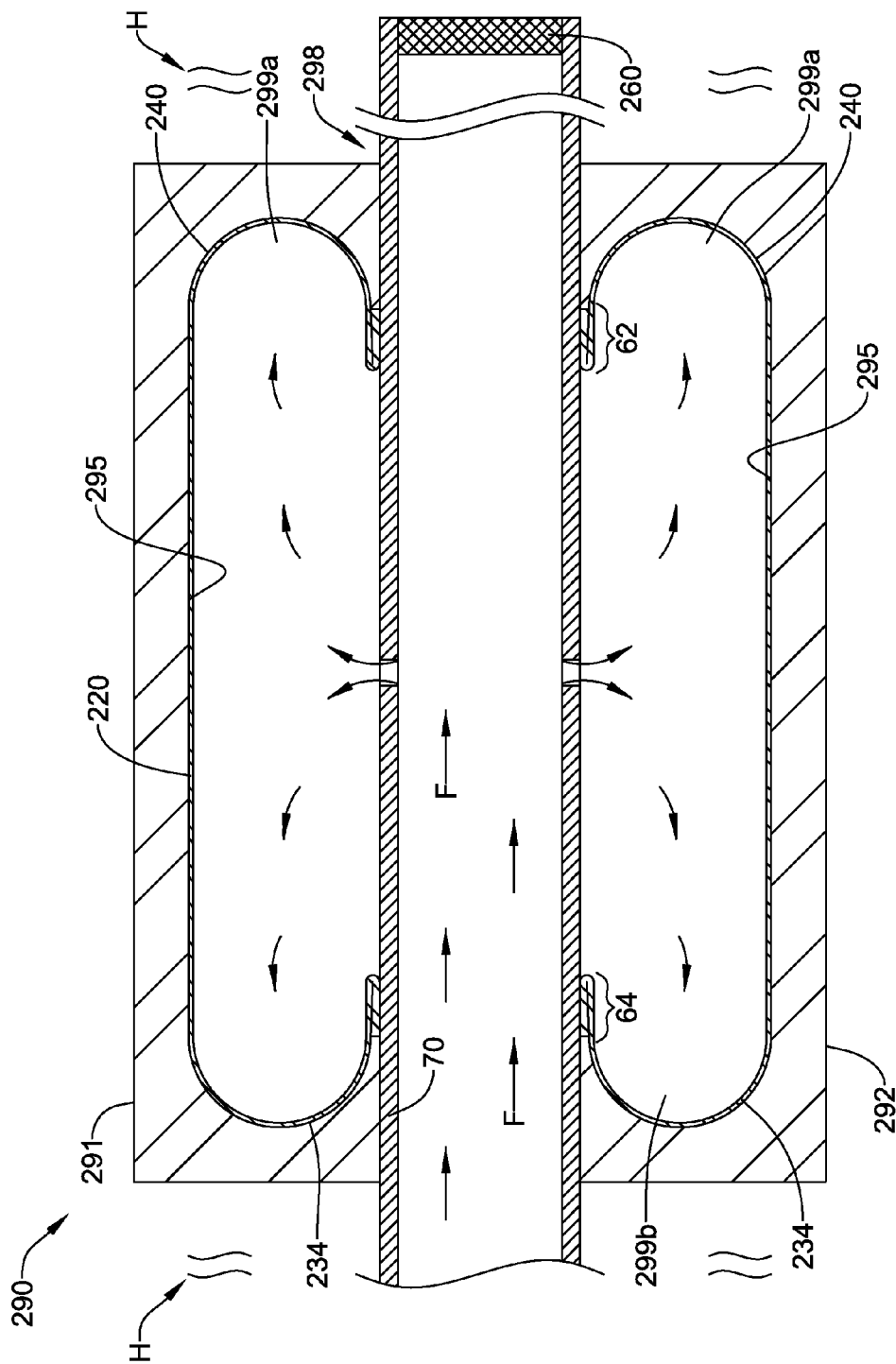

The balloon mold 290 may be closed around the tubular balloon parison 50 and the tubular catheter shaft component 70, and the tubular balloon parison 50 may be heated (shown by reference H in FIG. 14) to an elevated temperature to soften the polymeric material of the tubular balloon parison 50 to permit the tubular balloon parison 50 to be stretched during the balloon blow molding process, as shown in FIG. 14. For instance, the balloon mold 290 may be heated to an elevated temperature to heat the tubular balloon parison 50. In some embodiments, the balloon mold 290, with the tubular balloon parison 50 and the tubular catheter shaft component 70 positioned therein, may be placed in a heated liquid bath, or other heated chamber, to heat the tubular balloon parison 50 to an elevated temperature to soften the polymeric material of the tubular balloon parison 50 for the blow molding/stretching process. In other instances, heat may be applied by different means, such as induction heating, steam, hot air, etc.

With the tubular balloon parison 50 heated to an elevated temperature and softened, the annular space 74 between the tubular balloon parison 50 and the tubular catheter shaft component 70 may be pressurized with a fluid F to expand and stretch the tubular balloon parison 50 in the cavity 294 of the balloon mold 290 to form an inflatable balloon. For example, the fluid F may be directed to the annular space 74 by passing the fluid F through the lumen 75 of the elongate catheter shaft component 70 into the annular space 74 via the opening(s) 76 using a pressurization fixture. In some instances, a mandrel may be placed through the elongate catheter shaft component 70 during pressurization of the tubular balloon parison 50.

With the tubular balloon parison 50 at an elevated temperature, the tubular balloon parison 50 may be expanded and stretched to conform to the inner surface 295 of the cavity 294 of the balloon mold 290. As the tubular balloon parison 50 is expanded and stretched, the thickness of the tubular balloon parison 50 is reduced to create a pliable inflatable balloon from the tubular balloon parison 50. A portion of the tubular balloon parison 50 may stretch and expand distally of the distal bond region 62 to conform with the portion 299*a* of the cavity 294 distal of the rim 297*a* and distal bond region 62 to form an inflatable distal end portion 240 of the balloon 220 and/or a portion of the tubular balloon parison 50 may stretch and expand proximally of the proximal bond region 64 to conform with the portion 299*b* of the cavity 294 proximal of the rim 297*b* and proximal bond region 64 to form an inflatable proximal end portion 234 of the balloon 220.

Once the blow molding process is complete and the tubular balloon parison 50 has been blown and stretched to conform to the cavity 294 to form the balloon 220, the assembly may then be removed from the balloon mold 290. As shown in FIG. 15, the assembly, with the blown balloon 220 bonded to the catheter shaft component 70 may be used in a catheter assembly with the catheter shaft component 70 used as an outer tubular member 230 of the catheter shaft 212. As shown in FIG. 15, a distal portion of the tubular catheter shaft component 70 (e.g., the outer tubular member 230) may be removed (e.g., cut off) such that a distal end 242 of the tubular catheter shaft component 70 (e.g., the outer tubular member 230) is located at or proximal of the inflatable distal tip portion 240 of the balloon 220. Thus, the distal waist 238, formed by the distal bond region 62, may be an inverted distal waist extending proximally into the interior of the balloon 220 from a distal extent of the balloon 220, such that the inflatable distal tip portion 240 of the balloon 220 is the distalmost extent of the balloon 220.

Additionally, the proximal waist 236, formed by the proximal bond region 64, may be an inverted proximal waist extending distally into the interior of the balloon 220 from a proximal extent of the balloon 220, such that the inflatable proximal end portion 234 of the balloon 220 is the proximalmost extent of the balloon 220.

An inner tubular member 232, defining a guidewire lumen 222, may be positioned within the outer tubular member 230 and an inflation lumen 228 may be defined between the inner tubular member 232 and the outer tubular member 230. The inner tubular member 232 may be bonded (e.g., thermally or adhesively bonded) to the outer tubular member 230 at a bond region 278 proximate the distal ends of the inner tubular member 232 and the outer tubular member 230. The one or more, or a plurality of openings 76 extending through the outer tubular member 230 may permit fluid to pass from the inflation lumen 228 into the interior of the balloon 220. Thus, the balloon 220 may be sealingly affixed to the catheter shaft such that the interior of the balloon 220 is in fluid communication with the inflation lumen 228.

Furthermore, the inner tubular member 232 and/or the outer tubular member 230 may be attached (e.g., bonded) to a hub assembly having an inflation port in fluid communication with the inflation lumen 228 and/or a guidewire port in communication with the guidewire lumen 222.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of manufacturing a balloon catheter, comprising:
    attaching a first end region of a tubular balloon parison to an outer surface of an elongate tubular member of a catheter shaft to form a first bond region between the tubular balloon parison and the elongate tubular member of the catheter shaft;
    positioning the tubular balloon parison and the elongate tubular member in a balloon mold with the first bond region positioned in a cavity of the balloon mold;
    pressurizing an annular space between an inner surface of the tubular balloon parison and the outer surface of the elongate tubular member to expand the tubular balloon parison in the cavity of the balloon mold to form an inflatable balloon;
    removing the inflatable balloon and the elongate tubular member from the balloon mold; and
    attaching a waist of the inflatable balloon to the catheter shaft.

2. The method of claim 1, wherein a portion of the cavity of the mold into which the tubular balloon parison expands into is located distal of the first bond region.

3. The method of claim 1, further comprising:
    removing an end portion of the elongate tubular member extending from the first bond region.

4. The method of claim 1, wherein in the first end region of the tubular balloon parison forms an inverted waist of the inflatable balloon attached to the elongate tubular member.

5. The method of claim 1, wherein the waist of the inflatable balloon is attached to an outer tubular member of the catheter shaft surrounding the elongate tubular member.

6. The method of claim 5, wherein the outer tubular member is positioned over the elongate tubular member after removing the inflatable balloon and the elongate tubular member from the balloon mold.

7. The method of claim 1, wherein the waist of the inflatable balloon is attached to the elongate tubular member of the catheter shaft.

8. The method of claim 1, wherein an end portion of the tubular balloon parison is removed after expanding the tubular balloon parison to form the inflatable balloon and before attaching the waist of the inflatable balloon to the catheter shaft.

9. The method of claim 1, wherein the tubular balloon parison is heated to an elevated temperature during the step of pressurizing the annular space between the inner surface of the tubular balloon parison and the outer surface of the elongate tubular member to expand the tubular balloon parison in the cavity of the balloon mold to form the inflatable balloon.

10. A method of manufacturing a balloon catheter, comprising:
    extruding an elongate tubular member, the extruded elongate tubular member having an outer surface, an inner surface, and a length;
    extruding a tubular balloon parison, the extruded tubular balloon parison having an outer surface, an inner surface, and a length;
    positioning the extruded tubular balloon parison around the extruded elongate tubular member;
    securing a first end region of the extruded tubular balloon parison to the outer surface of the extruded elongate tubular member to form a first bond region between the extruded tubular balloon parison and the extruded elongate tubular member;
    positioning the extruded tubular balloon parison and the extruded elongate tubular member in a balloon mold with the first bond region positioned in a cavity of the balloon mold and an end portion of the extruded tubular balloon parison extending from the cavity of the balloon mold;
    pressurizing an annular space between the inner surface of the extruded tubular balloon parison and the outer surface of the extruded elongate tubular member to expand the extruded tubular balloon parison in the cavity of the balloon mold to form an inflatable balloon;
    removing the inflatable balloon and the extruded elongate tubular member from the balloon mold;
    removing the end portion of the extruded tubular balloon parison after expanding the extruded tubular balloon parison to form the inflatable balloon;
    positioning an outer tubular member over the elongate tubular member; and
    attaching a waist of the inflatable balloon to the outer tubular member.

11. The method of claim 10, wherein the first bond region is a distal bond region and a portion of the cavity of the mold into which the extruded tubular balloon parison expands into is located distal of the distal bond region.

12. The method of claim 10, further comprising:
  removing an end portion of the elongate tubular member extending from the first bond region.

13. The method of claim 10, wherein the first end region of the tubular balloon parison forms an inverted waist of the inflatable balloon attached to the elongate tubular member.

14. The method of claim 10, wherein the extruded tubular balloon parison is heated to an elevated temperature during the step of pressurizing the annular space between the inner surface of the extruded tubular balloon parison and the outer surface of the extruded elongate tubular member to expand the extruded tubular balloon parison in the cavity of the balloon mold to form the inflatable balloon.

15. A method of manufacturing a balloon catheter, comprising:
  bonding an inner surface of an extruded tubular balloon parison to an outer surface of an elongate tubular member of a catheter shaft to form a first bond region between the extruded tubular balloon parison and the elongate tubular member of the catheter shaft;
  positioning the extruded tubular balloon parison and the elongate tubular member in a balloon mold with the first bond region positioned in a cavity of the balloon mold and a portion of the extruded tubular balloon parison extending out of the balloon mold;
  pressurizing an annular space between the inner surface of the extruded tubular balloon parison and the outer surface of the elongate tubular member to expand the extruded tubular balloon parison in the cavity of the balloon mold to form an inflatable balloon;
  removing the inflatable balloon and the elongate tubular member from the balloon mold; and
  securing a proximal hub assembly to a proximal end of the catheter shaft.

16. The method of claim 15, further comprising:
  positioning an outer tubular member over the elongate tubular member; and
  bonding a proximal waist of the inflatable balloon to a distal end portion of the outer tubular member.

17. The method of claim 16, further comprising:
  securing the proximal hub assembly to a proximal end of the outer tubular member.

18. The method of claim 15, wherein a portion of the extruded tubular balloon parison is bonded to the elongate tubular member at the first bond region forms an inverted distal waist of the inflatable balloon bonded to the elongate tubular member.

19. The method of claim 15, further comprising:
  bonding the inner surface of the extruded tubular balloon parison to the outer surface of the elongate tubular member of the catheter shaft to form a second bond region between the extruded tubular balloon parison and the elongate tubular member of the catheter shaft, the second bond region being spaced away from the first bond region with the annular space defined therebetween.

20. The method of claim 15, wherein a portion of the cavity of the mold into which the extruded tubular balloon parison expands into is located distal of the first bond region.

* * * * *